(12) United States Patent
Linti et al.

(10) Patent No.: US 8,032,199 B2
(45) Date of Patent: Oct. 4, 2011

(54) GARMENT WITH INTEGRATED SENSOR SYSTEM

(75) Inventors: Carsten Linti, Stuttgart (DE); Heinrich Planck, Nurtingen (DE); Hansjurgen Horter, Oberboihingen (DE); Ursula Gutknecht, Lichtenstein (DE)

(73) Assignee: DITF Deutsche Institute fur Textil-und Faserforschung, Denkendorf (DE)

( * ) Notice: Subject to any disclaimer, the term of this patent is extended or adjusted under 35 U.S.C. 154(b) by 1222 days.

(21) Appl. No.: 11/630,501

(22) PCT Filed: Jun. 17, 2005

(86) PCT No.: PCT/EP2005/006544
§ 371 (c)(1),
(2), (4) Date: Jan. 22, 2007

(87) PCT Pub. No.: WO2006/000345
PCT Pub. Date: Jan. 5, 2006

(65) Prior Publication Data
US 2008/0091097 A1    Apr. 17, 2008

(30) Foreign Application Priority Data
Jun. 23, 2004  (DE) .......................... 10 2004 030 261

(51) Int. Cl.
*A61B 5/0402* (2006.01)
*A61B 5/0205* (2006.01)
(52) U.S. Cl. ........ 600/388; 600/389; 600/393; 600/484; 600/534; 600/547; 600/549

(58) Field of Classification Search .................. 600/388, 600/389, 393, 484, 534, 547, 549
See application file for complete search history.

(56) References Cited

U.S. PATENT DOCUMENTS

| | | | |
|---|---|---|---|
| 4,748,433 A | 5/1988 | Jackson et al. | |
| 4,960,118 A | 10/1990 | Pennock | |
| 4,966,155 A * | 10/1990 | Jackson | 600/484 |
| 5,295,490 A | 3/1994 | Dodakian | |
| 6,461,307 B1 * | 10/2002 | Kristbjarnarson et al. | 600/534 |
| 6,551,252 B2 * | 4/2003 | Sackner et al. | 600/388 |
| 6,970,731 B1 * | 11/2005 | Jayaraman et al. | 600/388 |
| 7,173,437 B2 * | 2/2007 | Hervieux et al. | 600/388 |
| 7,308,294 B2 * | 12/2007 | Hassonjee et al. | 600/386 |

FOREIGN PATENT DOCUMENTS
CN     1274270 A    11/2000
GB     2166871    *  5/1986

OTHER PUBLICATIONS

"Fabric Sensors for the Measurement of Physiological Parameters", the 12th International Conference on Solid State Sensors, Actuators and Microsystems, Boston, Jun. 8-12, 2003, pp. 1-4.

* cited by examiner

*Primary Examiner* — Lee Cohen
(74) *Attorney, Agent, or Firm* — Leydig, Voit & Mayer, Ltd

(57) ABSTRACT

A garment preferably in the form of a body suit which carries one or more sensors for sensing bodily functions of a wearer of the body suit. The body suit preferably has stretchable sections or belts upon which the sensors are carried such that the sensors are maintained in proper position on the body for reliable detection of the body functions.

54 Claims, 9 Drawing Sheets

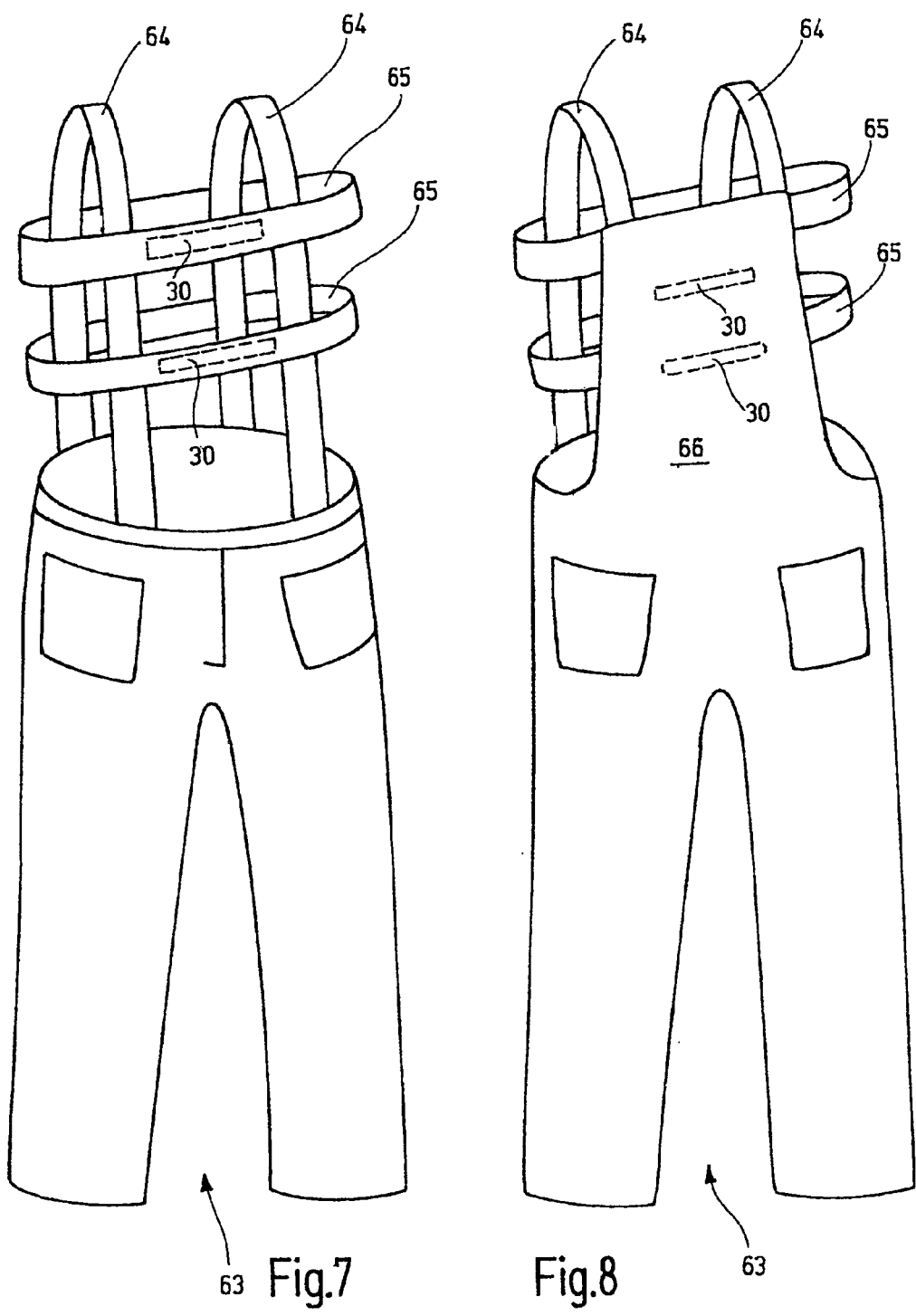

GARMENT WITH INTEGRATED SENSOR SYSTEM

FIELD OF THE INVENTION

The present invention relates to garments, and more particularly, to garments that enable monitoring of bodily functions of the wearer of the garment.

BACKGROUND OF THE INVENTION

In a number of illnesses or situations, it is expedient to continuously monitor the person or patient for diagnostic and therapeutic purposes. The monitoring involves cardiac functions of respiration, skin resistance, transpiration, body temperature and the like. Depending on the type of illness or situation being monitored, a differing mix of parameters can be required. The measurement should be done continuously over a long period of time, and not just for a few minutes. This requires that sensors placed on the body not significantly impair the comfort and the normal freedom of movement.

Situations in which monitoring of the vital parameters is necessary can occur during various phases of life. For example, in medically warranted cases one must detect irregular breathing or heart defects or support rehabilitation procedures (care of the elderly, telemedicine, etc.). In work safety situations, monitoring is necessary to preclude overexertion or unacceptable risk. In fitness, sports or wellness activities, one can keep a record of the training results or support the training by means of a monitoring.

Infants and small children are especially difficult to monitor, as they have a more pronounced motor activity. In any case, the sensors must be held in constant contact with the body to preclude measurement errors. On the other hand, the electrical leads of the sensors must not present a danger to the person or the small patient being monitored.

OBJECTS AND SUMMARY OF THE INVENTION

It is an object of the present invention to provide a garment that facilitates maintaining of one or more sensors in proper position on a human body for monitoring body functions. Pursuant to the invention, a sensor supporting garment is provided that is made of a material that can stretch in at least one direction. Due to the stretching ability, movement of a person wearing the garment is relatively unimpaired and, on the other hand, the stretching ability ensures that the sensor or sensors remain in adequate contact with the body. The tailoring is such that the garment, when placed on the body, remains fixed in proper position.

The garment contains at least one sensor for detecting a vital function, such as skin resistance, transpiration, respiration, pulse, action currents of the heart, body temperature and the like. The sensors generate an electric signal, which is either an unmodified input electric signal, or they serve as an interface for diverting the electric currents of the body into a measuring instrument. For this purpose, moreover, a connection cable, which is led out from the garment is secured inside the garment.

It is especially desirable for the garment to be in the form of a so-called body suit, enclosing the chest and abdomen, while being provided with a neck, arm and leg cutouts. To facilitate dressing of an infant or small child with such a body suit, the body suit can be opened in the lengthwise direction. Furthermore, it is advantageous for the body suit to have a crotch piece tailored as one piece with the garment, running across the crotch.

In particular, and again for infants and small children, it is advantageous to provide the body suit with sleeves, which serve not only to carry sensors, but also to form a complete garment, protecting the body from getting a chill. However, it also is possible to configure the garment as a vest, in the form of a T-shirt, or an undershirt with straps. If the material of the garment is elastically stretchable in all directions, the garment can be adapted very well to the shape of the wearer without causing significant constraint or folding when the wearer is moving.

In a particularly desirable form, the material of the garment is a multilayered woven fabric. The multilayered woven fabric is preferably a knitted fabric, which in itself provides the necessary elasticity. The material for the knitted fabric can be ordinary cotton, possibly containing spandex threads to a slight degree, such as less than 5%. The cotton threads substantially improve the wearing comfort. Rayon, synthetic or microfibers can be used and can substantially broaden the function of the textile in some situations, as they have a climate control action, alleviating skin complaints such as neurodermitis or the like.

The sensors can be of a type that their resistance value is altered when stretched. Preferably, the specific resistance of the sensor is 25 ohm cm, or the value can be in a range between 5 ohm cm and 30 kohm cm.

With such a stretching-dependent sensor, the original electric signal is modified, since the current flowing through the sensor is increased or decreased according to the resistance value. When the sensor is supplied with constant current, it is the voltage drop that is altered, which in that case serves as the signal.

A stretching-dependent sensor can also be created by using a nonconductive elastomeric base material in which conductive particles are embedded. The conductive particles can be carbon particles or conductive metal particles, i.e., metal particles which have not formed a nonconductive skin on their surface by oxidation or do not form such within a very short time, even when embedded in the elastomer. Another form of a stretching-dependent sensor can be based on a hydrogel material.

The elastomer is preferably a skin-tolerated elastomer, which at least for the most part is nonallergenic. This condition is of special importance only in the case of a sensor worn directly on the skin, such as sensors or electrodes for tapping the action currents of the heart or measuring the skin resistance.

Preferably, the elastomer can stretch more than the substrate on which the sensor is found. In this way, the stretching capacity of the sensor will not restrict that of the substrate, in this case, the garment or part of the garment. Suitable materials for the substrate are fluoroelastomers, polyurethanes or silicone.

Depending on the application, it can be advantageous to provide the sensor with a stretchable insulating layer on at least one side. This can be, for example, an intermediate layer between the actual active surface and the substrate in the form of the garment, or it can be an insulating layer between the active part of the sensor and the skin in the case of elongation sensors. In order for moisture not to influence the measurement signal in the case of elongation sensors, the active layer of these sensors can be surrounded on all sides by insulating layers. In any case, the insulating layers can consist of the same base material as the active layers. In order to utilize the electrical signals, the sensor is hooked up to at least one lead wire. In the case of elongation sensors, two lead wires are necessary.

Good electrical signals are obtained in the case of elongation sensors when the elongation sensor is configured as a web, i.e., the transverse dimension is small relative to the longitudinal dimension. The sensitivity can be even further enhanced if the web of the sensor extends at least once in a U-shape, with a Z-shape also being considered a multiple U-shape. In this way, the longitudinal extent of the elongation sensor can be shorter as compared to an elongation sensor that has only one web in the longitudinal direction and the same sensitivity.

In the case of sensors for tapping the action currents of the heart, which basically serve only as contact surfaces, a two-dimensional configuration on the side facing the body is advantageous. The shape can be round or angular, depending on the requirements. One should achieve a large contact surface without producing elongations that significantly influence the resistance value of the sensor.

The sensor must be so flexible and drapable as to conform well to the body surface. The surface can be smooth or structured. The structure can be composed of pyramids or tetrahedra so that sweat can be more easily drained from it. The tips increase the local contact pressure on the skin and thus create better local skin contact. However, the structure should not be too pronounced as this could result in damaging the skin and an unpleasant feeling when worn.

The sensor should consist of a material that is not sensitive to body sweat and transpiration. This insensitivity should exist for at least the surface layers provided they can adequately protect the core.

In order that the sensor does not impair the cleaning of the garment and/or its disinfection and/or sterilization, the sensor should consist of materials that are wash-resistant under normal conditions to allow for easy care, hot-water-fast to allow extensive disinfection, or even heat-resistant sufficient enough to withstand sterilization in an autoclave.

In order to keep the sensor in the closest possible contact with the body, the sensor can be placed in or on an at least partially stretchable belt, preferably an elastically stretchable belt. The belt can be a flat-lying tube, which can be formed as a plain or hosiery tube knit. This has the advantage that no seams occur which would impair the wearing comfort, for example, by rubbing against the skin, or impairing the stretchability. Furthermore, the tubelike belt can accommodate and protect the sensor, as long as no direct skin contact is required.

The belt preferably consists of a knitted fabric, enabling stretchability in the lengthwise direction of the belt. Thus, the belt is not constrictive. Neither chest breathing nor abdominal breathing of the patient or person being monitored is affected. The belt runs in the garment transversely to the longitudinal axis of the body when, for example, the breathing is being monitored. When two belts are present in the garment, one can monitor both the chest breathing and the abdominal breathing. A stretchable woven or nonwoven fabric can also be used as the material for the belt. Stretchable threads can be laid onto, sewn into or embroidered onto the woven or nonwoven.

The belt also can be produced in a single manufacturing step along with the textile (special sewing, knitting or weaving techniques are suitable for this, namely, so-called fully fashioned ones), wherein regions of the textile, i.e., the belt regions with adapted stretching qualities, can be formed. The stretching in the back can be less than the stretching in the chest and abdominal area.

The flat knitting technique, as well as heald shaft and Jacquard weaving techniques, make it possible to incorporate functions like changing stiffness and locally varying inserts of different materials into the surface. In the case of knitting, float stitches with top or bottom pads are possible. In the case of weaving, this is made possible by weaves such as linen, twill, or open. "Fully fashioned", as used herein, means a flat knitting technology allowing one to make a garment in a single work step, without later sewing steps. Due to rehanging of stitches and other techniques, in the "fully fashioned" technology one can also achieve other configuration possibilities beyond weaving and figuring, in addition to the overall layout. Thus, the belt can be integrated directly when making the garment, without additional cutting and sewing work. By selecting the stitch formation, the stitch width and the yarn, properties varying in wide ranges can be created.

To prevent the belt from shifting in the garment, the belt preferably is at least partly sewn to the garment. Other portions can be left free so that the belt can be pulled tight regardless of the fit of the garment. To close the belt, a snap button or a Velcro strip can be provided on it. The protection of the connection lines is improved if the belt emerges into a tubelike region of the garment, through which the connection cable is led.

Single conductors can be used for the electrical connection of the sensors to the evaluating electronics, each being insulated separately. These single conductors can be incorporated into a woven fabric, namely, as the warp threads. In this way, one achieves a robust flat ribbon cable, which is very flexible, and which can hardly twist because of the corresponding width. At the same time, the essentially nonstretchable, nonconducting warp threads protect the sensitive wires against overstretching, tearing or breaking on account of too sharp a bending radius. The insulated single conductors can also be incorporated in the knitted fabric as stationary threads.

The contacting with the sensors integrated into the textile or placed on the textile can be done by garment industry methods. For this, conductor tubes for stress relief, zig zag tubes to increase the stretching capacity, and ends with the insulation stripped off can be sewn, embroidered, glued, or welded onto the textile by known techniques. At the stripped and conductive ends of the cable, the sensors can be glued, soldered, knitted, sewn, welded or applied by coating. Some of these work steps can also be performed together so as to carry out the conductive contacting and any necessary insulation in a single work step.

Other objects and advantages of the invention will become apparent upon reading the following detailed description and upon reference to the drawings, in which:

BRIEF DESCRIPTION OF THE DRAWINGS

FIGS. 7 and 8 are front and rear perspectives of a pair of trousers with integrated sensors in accordance with the invention;

Figure 1:
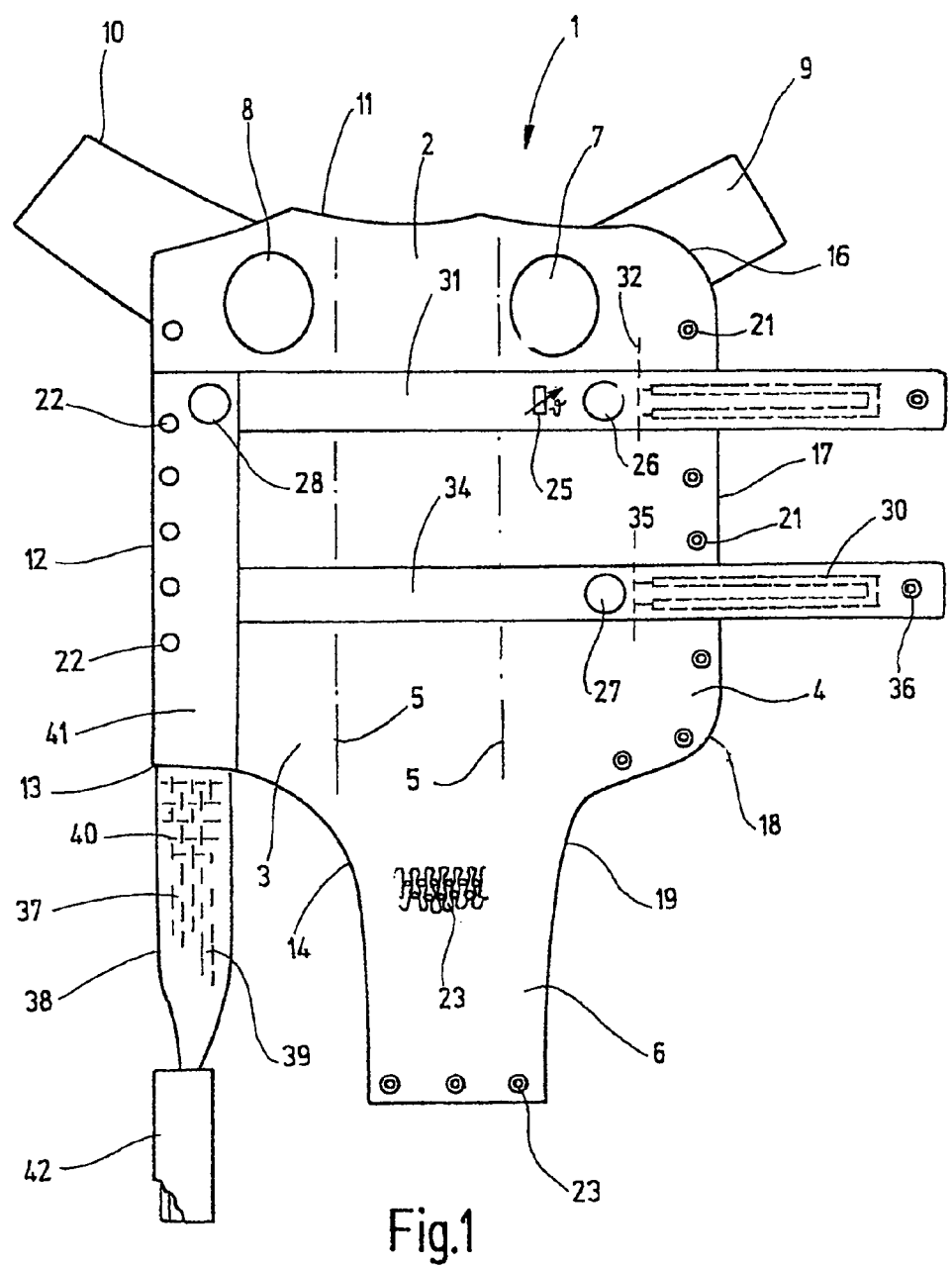
FIG. 1 is a plan view of a body suit in accordance with the invention, especially suited for an infant, shown in an unfolded condition looking at the interior.

While the invention is susceptible of various modifications and alternative constructions, certain illustrative embodiments thereof have been shown in the drawings and will be described below in detail. It should be understood, however, that there is no intention to limit the invention to the specific form disclosed, but on the contrary, the intention is to cover all modifications, alternative constructions, and equivalents falling within the spirit and scope of the invention.

DETAILED DESCRIPTION OF THE INVENTION

Referring now more particularly to FIG. 1 of the drawings, there is shown an illustrative body suit 1 in accordance with the invention which in this case particularly adapted for use with infants and small children. The illustrative body suit 1, which is shown in the unfolded condition looking at the inside, includes a back piece 2, which extends as a single piece into a right front piece 3 and a left front piece 4. The two front pieces 3, 4, are shown separated from the back piece 2 by imaginary broken lines 5. In a practical embodiment, the two front pieces, 3, 4 are tailored with no lateral seam. The terms "front piece" and "back piece" are used herein the traditional parlance of the garment industry.

At the lower end of the back piece 2, a flap or crotch piece 6 is tailored which passes through the crotch when wearing the garment. At the upper end of the two front pieces 3, 4 arm cutouts 7, 8 are formed from which sleeves 9, 10 emerge, which are sewn about the cutouts 7, 8. An upper edge 11 forms a neck cutout when in the wearing condition.

The right front piece 3 is bounded at the side by a straight edge 12, which starts at the upper edge 11 for the neck cutout and extends to the crotch piece 6 at approximately at pant 13, i.e., at a height characterizing the transition between the back piece 2 and the crotch piece 6, with a curved tailored edge 14. The left front piece 4 passes with a rounded edge 16 into a straight, downward running edge 17, which in turn passes at the height of the corner 13 in a rounded segment 18 into the curved edge 19, which at the same time also represents the side boundary of the crotch piece 6. The transverse dimension of the front piece 4 is larger than that of the front piece 3 so that when worn the front piece 4 can fold across the side of the front piece 3 away from the body.

To secure the body suit 1 in the closed condition, snap button top halves 21 are provided along the edges 17, 18. The snap button top halves 21 correspond to snap button bottom halves arranged along the tailored edge 12. The snap button have bottom halves in the form of rivet rings 22, which are used to secure the snap button halves to the body suit 1.

Additional snap button top halves 21 are present on the lower free end of the crotch piece 6. These correspond to snap button top halves that are sewn onto the outside of the two front pieces 3, 4 which are not visible in the figure. Instead of the snap buttons shown, buttons, hooks or tentacle closures alternatively could be provided to close the textile garment.

In carrying out the invention, the body suit 1 serves to support the sensors in a manner for reliably monitoring vital functions of the wearer. The sensors in this case include a temperature sensor 25, three electrodes, 26, 27, 28 for tapping action currents of the heart in two channels, and two strain gage measuring strips 29, 30, indicated by broken lines in FIG. 1, to detect the chest breathing and abdominal breathing. Additional sensors in the form of electrodes can be included to measure the skin resistance or the transpiration.

The base material for the body suit 1, including the arms 9, 10, consists of a knitted fabric. The knitted fabric can be a tricot, a hosiery knit, or a knit fabric. The advantage of the knitted fabric is that the textile fabric can stretch in both axial directions and has a certain recoil ability. Due to this property, a tighter fit is assured without a tendency to form folds during movement. The fit to the body can be further improved by knitting in yet another elastomeric thread, for example spandex, to a slight extent. The method of knitting in spandex threads is known in the art and thus need not be discussed in detail.

The elongation measuring strip 29 is located in a belt 31, which is designed as a knitted tube. The stitch wales lie in the lengthwise direction of the belt 31. The belt 31 is sewn to the body suit 1 at approximately one site 32, indicated by a broken line. The belt 31 starts in the vicinity of the edge of cut 12 and reaches, as shown, across the edge of cut 17. It lies perpendicular to the lengthwise axis of the human body when the body suit 1 is being worn. Furthermore, it is dimensioned such that when the body suit is worn it is led out from between the two front pieces 3, 4. To fasten the free end of the belt 31, another snap button 33 is provided, corresponding to snap button sockets located on the outside of the front piece 3 or the back piece 2 which in this instance are concealed in the drawing by the belt 31.

Since the belt 31 is designed as a tube, the elongation measuring strip 29 can be located on the inside of the belt, which helps protect the strip 29 from mechanical damage. Moreover, skin irritation which might be caused by the elongation measuring strip and its edges is also avoided since there is a layer of fabric between the skin of the wearer and the elongation measuring strip 29. The material of the fabric can be the same material as used for the main part of the body suit 1, namely, essentially cotton or any skin-tolerated fabric based on synthetic fiber that ensures good wearing comfort and takes up moisture.

In the vicinity of the arm cutout 7, the electrode 26 is located on the belt 31, as shown. It is placed such that when the body suit 1 is worn, the electrode lies against the body at the location which can be utilized in electrocardiography. The second electrode 28 is likewise located in a prolongation of the belt 31 at the same body height.

Another belt 34 runs transversely to the back piece 2 at a height corresponding to just above the belly button of the user in the worn condition. The belt 34 is constructed the same as the belt 31 and it is secured in similar fashion. The tubelike belt 34 is sewn firmly to the right front piece 3, the back piece 2 and the left front piece 4 up to a point 35. The adjoining segment forms a free lap piece, containing the elongation measuring strip 30. The free end of the belt 34 is provided with a snap button 36 for keeping the belt under tension against the body of the wearer. The belt 34 also has an electrode 27 for tapping the action currents of the heart. Its position corresponds to the position required for the two-channel tapping of heart currents.

Extremely fine, insulated wires, as shown by broken lines 37 in FIG. 1, are used for tapping the electrical signals from the electrodes 26, 27, 28, the thermistor in the form of an NTC resistor 24 (25?), and the two elongation measuring strips 29, 30. These wires, because of their fineness, are extremely fragile. In order to protect them mechanically, they are part of a fabric strip 38, which is woven as a strip with closed edges which cannot become frayed. In this strip, the insulated wires 37 form parallel warp threads alongside each other. To the right and left of these centrally located electrical wires there are woven in warp threads 39 consisting of cotton or synthetic fiber which for the most part is not stretchable. Weft threads 40 of the strip 38 also consist of unstretchable cotton, synthetic or mixed fibers.

The ribbon cable obtained in this way runs next to the edge of cut 12, being covered by a sewn-on flap 41. At the height of the belt 34, a first segment branches off at right angles, runs into the belt 34, and makes appropriate contact there. Another part of the ribbon cable 38 bends over, roughly underneath the electrode 28, in order to make contact with the sensors contained in the belt 31, including the electrode 28. The lower free end of the striplike cable is provided with a plug 42 in order to connect the sensors electrically to an evaluating electronic system.

Due to the special arrangement of the striplike cable 38, it runs when worn through the center of the body in the direction of the legs, thereby producing the least possible hindrance, and also minimizing the risk of the cable getting torn by the movements of the wearer, especially an infant. It can be led out in the leg cutout and does not hinder the infant in its natural movement, even if the child is rather big and is turning in bed. There is no risk of strangulation.

At the same time, the body suit 1 by completely enveloping the thorax and abdomen ensures that the various sensors remain placed at the proper location on the body. They cannot shift in either the circumferential direction or the longitudinal direction. The pretensioning also ensures the necessary contact pressure so that the electrical connection between the electrodes 26, 27, 28 and the skin surface remains in place. The tight fit of the belts 31, 34 means that the elongation measuring strips 29, 30 will also transmit the expansion resulting from chest and abdominal breathing. This ensures proper monitoring of the wearer's breathing.

Figure 2:
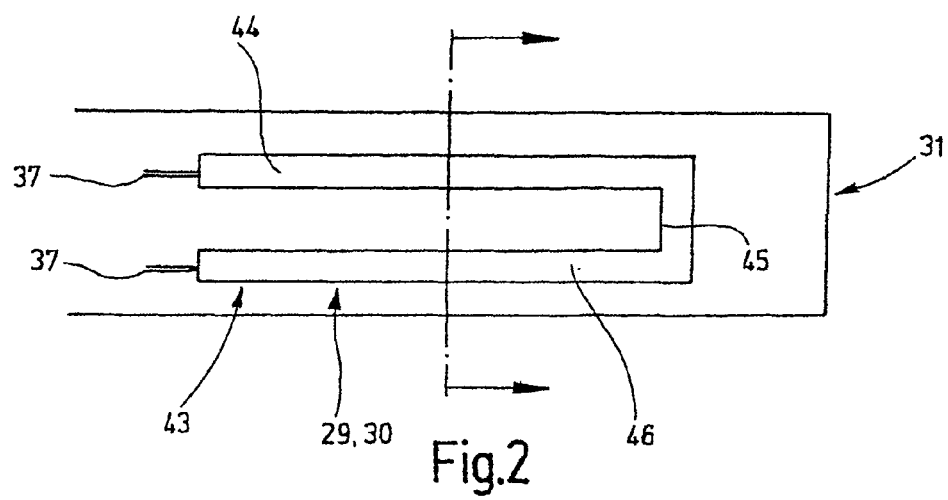
FIG. 2 is an enlarged top view of one of the elongation sensors of the illustrated body suit.

The elongation measuring strip 29, 30 is shown in detail in FIG. 2. FIG. 2 reveals the cut-open tubelike belt 31, with a U-shaped strip 43 being arranged on the side of the flat side of the tube facing the body of the wearer. The strip 43 has a first leg 44 parallel to the lengthwise dimension of the belt 31. At the end corresponding to the free end of the belt 31, the first legs 44 connects with a back segment 45, which connects to a leg 46 that extends parallel to the leg 44. At the free ends of the two legs, the corresponding electrical lines 37 are hooked up.

Figure 3:
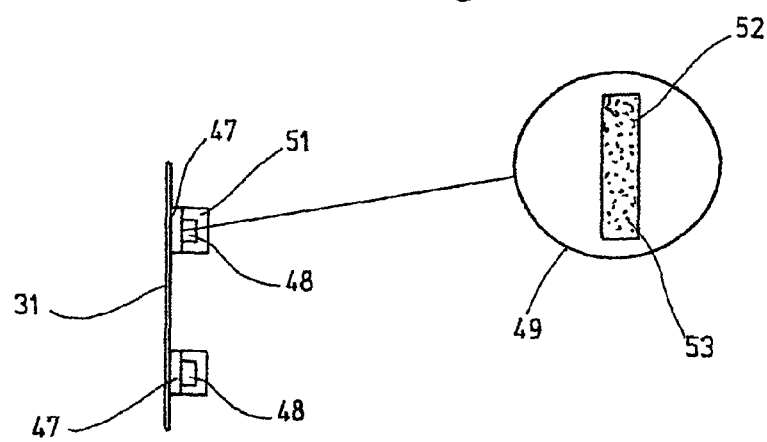
FIG. 3 is a transverse section of the elongation sensor shown in FIG. 2, taken in the plane of line 2-2.
Figure 4:
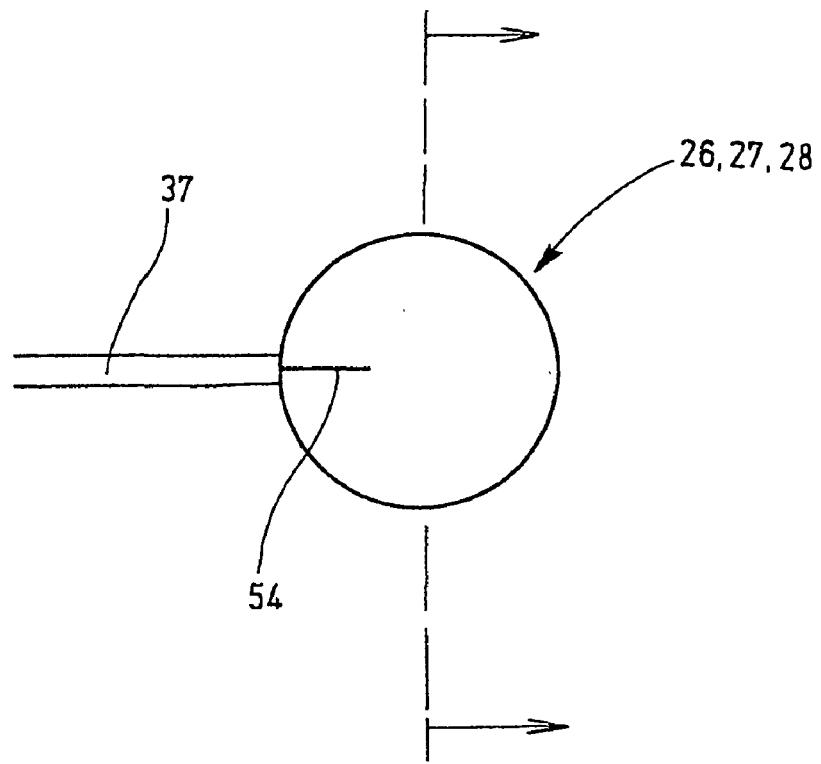
FIG. 4 is an enlarged depiction of a cutout from a flat ribbon cable for connecting to the sensor.
Figure 5:
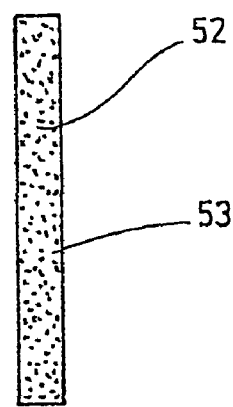
FIG. 5 is an enlarged vertical of a sensor or an electrode of the illustrated body suit for tapping or monitoring action currents of the heart or for measuring skin resistance.

The construction of the elongation measuring strip 29, 30, as shown in the cross section in FIG. 3, includes an insulating layer 47 arranged on the inside of the belt 31. The insulating layer 47 follows the course of the strips 44, 45, 46. The insulating layer 47 is insulating in the electrical sense, i.e., it is extremely high-resistive.

In the middle, an electrically conductive layer 48 is arranged on the insulating layer 47. The electrically conductive layer 48 is narrower than the insulating layer 47 and continues uninterrupted the entire length of the strips 44, 45, 46. The internal construction is shown enlarged at 49.

The electrically conducting layer 48 is covered by another insulating layer 51, as can be seen from the cross sectional drawing in FIG. 3. In this way, the electrically conductive layer 48 is enveloped on all sides and makes electrical contact only at the ends of the strips 44, 46 via the conductors 37.

The material for the layers 47, 48, 51 is an elastomer which is skin-tolerable and also preferably nonallergenic. Suitable materials are polyurethane, silicone and fluoro-elastomers. Moreover, these elastomers have the property of being very stretchable and not hindering the stretching ability of the belt 31, which serves as a substrate for the elongation measuring strips 29, 30.

The elastomers used have a greater stretching ability than the textile substrate on which they are fastened, protects the elastic structure against overstrain. The elastomers, for example in the case of silicone, are distinguished by very slight rigidity and a low Shore A-hardness of less than 20. If the layer has a slight thickness of less than 1 mm, the stretching of the textile substrate will be insignificantly hindered by the elastomer.

Furthermore, the elastomer, depending on the application, should be at least warm water resistant so that the body suit can be washed. In the case of higher requirements for sterility, hot water resistance may also be required in order to disinfect the body suit 1. If necessary, a sterilization in the autoclave might even be desired, which further increases the demands on the temperature and steam resistance of the elastomers. The same holds, of course, for the insulation of the connection wires 37.

Since the above-mentioned elastomers are essentially electrical nonconductors, the conductivity of the central conductive layer can only be maintained by embedding conductive particles, such as carbon particles 52, in an appropriate amount. The carbon particles are embedded in a proportion such that a specific resistance of around 25 ohm cm is created. Preferably, the specific resistance varies in a range between 2 ohm cm and 1 kohm cm.

Due to the electrically conductive particles embedded in the elastomer, the specific resistance of the electrically conductive resistance layer 48 varies as a function of the stretching. Since the elongation measuring strip 29, 30 has a U-shaped configuration, a higher useful signal will be generated because two strips lying parallel to each other in the lengthwise direction will be stretched at the same time. The resulting signal is larger than if only one strip is used. An even greater sensitivity is achieved by having more than two strips in parallel with each other so long as space conditions permit. The contacting preferably occurs by embedding the ends of the connection wires 37 with the insulation peeled off in the not yet hardened elastomer of the resistance layer 48. Then the insulating elastomer layer 51 is placed on this.

In place of carbon particles, appropriate metal particles can also be used. The metal particles should remain electrically conductive inside the elastomer, even at the surface, and not be oxidized into a nonconductive layer at the surface.

The electrodes 26, 27, 28 are placed on the inner top side of the body suit as a conductive layer and have the shape of a circular disk with a diameter of around 1.5 cm. They are constructed in similar manner to the resistance layer 48, consisting of an elastomer 53 in which once again electrically conductive particles 52 are embedded. The connection wire 37 is embedded at one stripped end 54 in the not yet hardened elastomer mass and is thereby both electrically contacted and mechanically secured, as is also the case with the elongation measuring strips 29, 30.

The surface can be smooth or structured. In the case of a structuring, the surface consists of an arrangement of tetrahedra or pyramids or an imitation textile surface, which improves the transport of sweat, the wearing comfort, and the draping quality, as well as the contact resistance. The electrode can also be made entirely of textile by working electrically conductive yarn or threads into a textile surface. This surface can either be sewn on in the specified shape and size or be worked in as a tarsia when knitting the belt.

Since what is important for the electrode is not a change in resistance, but a lowest possible resistance, the proportion of electrically conductive particles 52 may be rather high (>50% by volume). Instead of carbon particles, metal particles again also can be used. In selecting the suitable material, however, the metal particles should not have any electrically insulating oxide layer, even after the hardening of the polymer. Otherwise, they would merely serve as a nonconducting filler which would defeat their purpose.

In the embodiment of FIG. 1, the body suit 1 can be produced, for example, by circular knitting, followed by cutting out and hemming of the edges. The connection cables are produced as separate strips and then sewn on.

Figure 6:
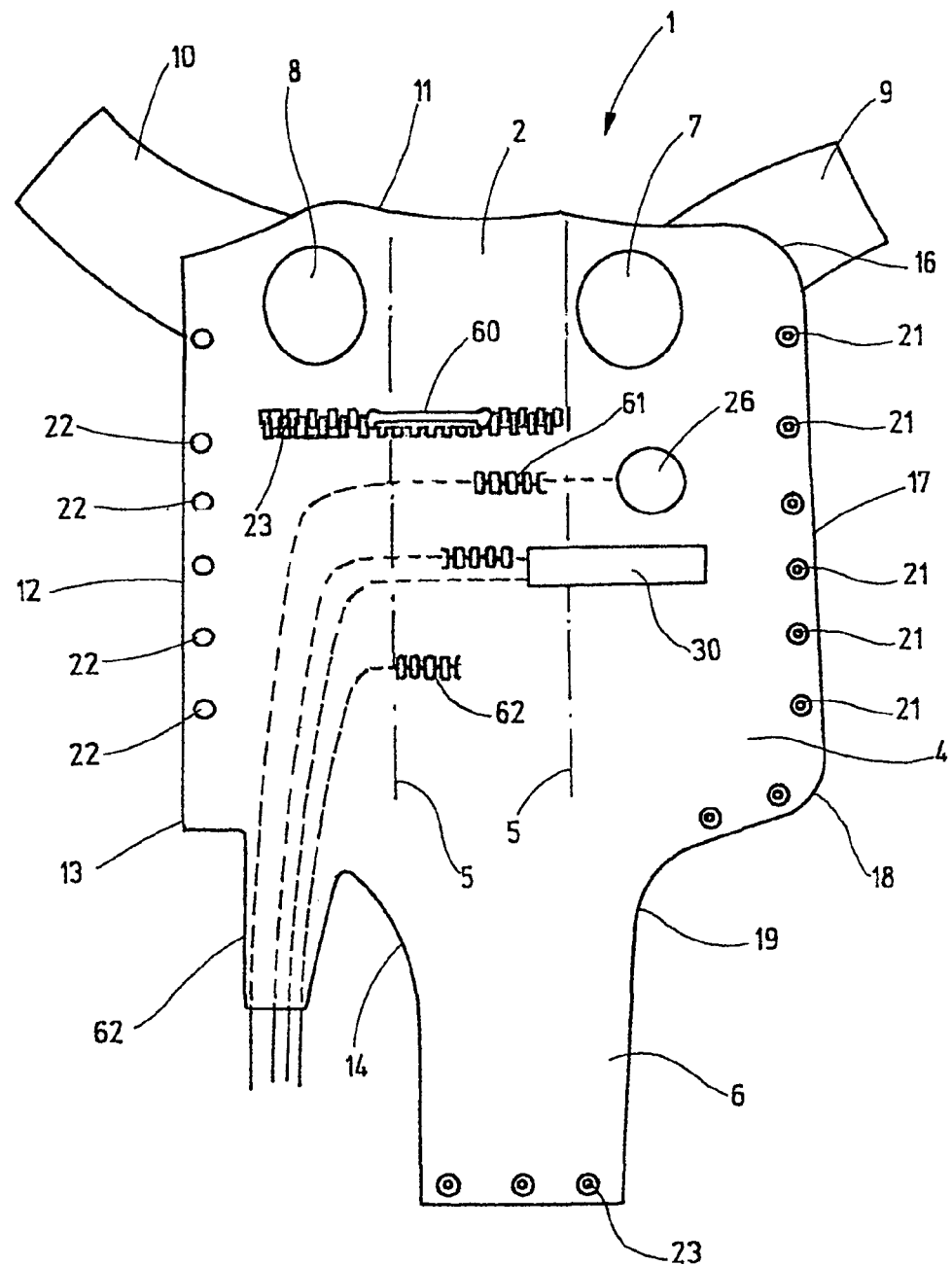
FIG. 6 is a plan view of an alternative embodiment of the body suit in which electrical lines are worked directly into the textile of the body suit.

FIG. 6 shows an embodiment produced by the so-called "fully fashioned" method. This is a special flatbed knitting technique in which the desired structure (except for the sleeves 9, 10) is produced in the particular desired form in a single work step.

One achieves a different stretching ability in the back region 2 because, as is shown, individual threads 60 lie there as a float in the knitted fabric 23, i.e., they are not knitted off. Float means in the garment industry that the threads lie in the direction of the stitch row without forming stitches. This reduces the stretching ability on account of the lack of a stitch structure.

Furthermore, it is possible, as shown at 61, to knit conductive threads in directly so as to achieve the contacting of the sensor 26. The knitted-in threads at first run in the direction of the stitch row, i.e., they form stitch rows, or they are stitched together with the base material as plaiting threads. In the vicinity of the side edge 12, these conductive threads that form the connection wires are then incorporated in the direction of the stitch wale, and emerge as free ends at a stitched-on bracket 62 so that they can make contact there at a plug, corresponding to the plug 42. An elongation sensor 30 is connected in a similar manner, in that several wires are knitted in at a distance from each other, and thus are electrically insulated from each other, in order to accomplish the electrical contacting.

Preferably several conductors are knitted in for each electrical line in order to achieve a certain redundancy so that the electrical contact is not lost if one of the conductors gets broken. In order that body sweat absorbed by the textile base material does not produce any unwanted short circuiting between the conductors, the wires each are insulated from each other and preferably are stitched in. Finally, special pattern techniques, as are known from the Jacquard process, can be used to knit in structures, as indicated at 62, in order to achieve, for example, a shiny metal contact surface.

The advantage of the technique for making the body suit as shown in FIG. 1 lies in the lesser requirements in the complexity of the knitting and weaving machines used. On the other hand, a number of cutting and sewing steps are necessary. The cutting and sewing work is significantly reduced in making the body suit in FIG. 6. On the other hand, more complicated textile machines are required.

The fundamental principle of the invention has been explained above by means of a body suit. This body suit can be used for infants, small children, or even adults. The essential benefit is that it can be used both for bedridden patients/persons, and it can also be worn during normal activity or sports.

Another implementation of the invention is depicted in FIGS. 7 and 8, which illustrates the type of garment by means of which the monitoring is carried out is not limited to body suits. Instead, FIG. 7 shows pants 63 which are supported by means of suspenders 64 which are joined to each other by belts 65. The belts 65 carry sensors 30, shown by broken line, on the side facing the body. The belts, in turn, run in the direction transverse to the lengthwise axis of the body and lie against the body due to their natural elasticity. Additional sensors can easily be placed on the side of the suspenders 64 facing the body. Due to the pretensioning of the belt 65 running in the chest region, the suspenders are likewise held in close fitting relation against the surface of the body in order to take measurements in a manner similar to that explained in connection with the body suit in FIG. 1.

FIG. 8 shows overalls with a bib 66 on which sensors 30 are placed on a side facing the body. The belts 65 emerge sideways from the bib 66 and surround the body of the wearer. They elastically press the bib 66 with the sensors 30 located on its inner side against the skin surface, similar to that described above. Furthermore, suspenders 64 emerge from the top edge of the bib 66 and lead to the waistband of the pants 63. The natural weight of the lower part of the pants 64 prevents the sensors arranged on the suspenders 64 of the belts 65 from shifting upward in undesirable manner while being worn and leaving their prescribed location on the body. It will be understood that the garments shown in FIGS. 7 and 8 are also especially suitable for monitoring the bodily functions of people carrying out their normal activity and requiring full mobility.

As shown in the embodiment of FIG. 1, a ribbon cable 38 is used for connecting the sensors 29, 30. This is woven as a flat ribbon with closed edges. At roughly the height of the belt 34, the ribbon cable is incised lengthwise, in order to produce the F-shape by folding over. When a large number of sensors or electrodes need to be connected, it might be difficult to accommodate the many wires as warp threads in one plane, such as occurs in a simple flat strip.

Figure 9:
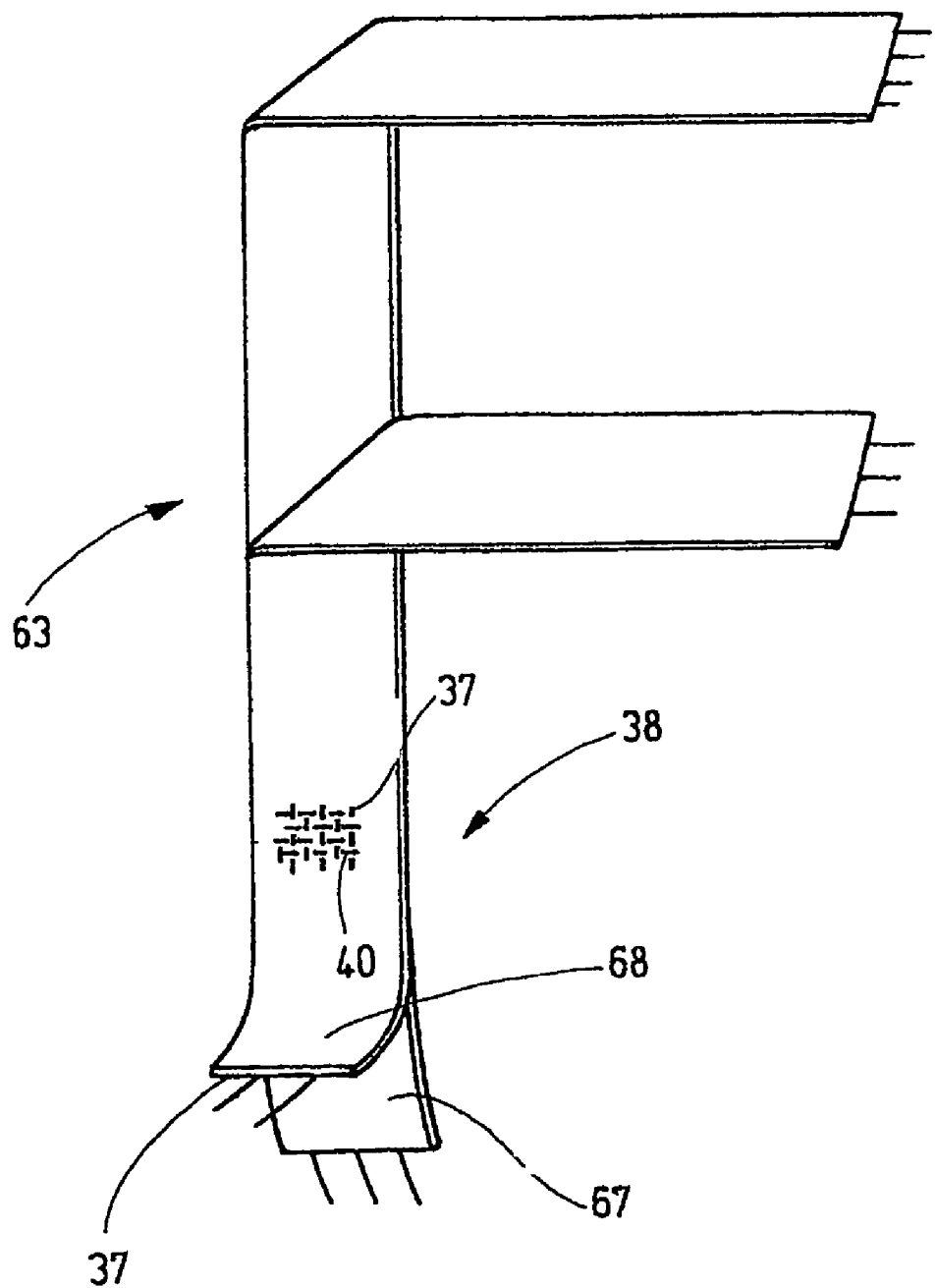
FIGS. 9-11 are perspectives of alternative embodiments of ribbon cables that can be used with the garment sensors of the present invention.

For a very large number of connection lines or wires, the structure as in FIG. 9 is especially suitable. In this case, the connection cable 38 consists of a woven tube. Such a woven tube is endless in the circumferential direction and forms two imaginary strips 67, 68, which are joined together as a single piece along their two margins by spirally running weft threads. In this way, a two-ply formation is created, and connection wires 37 can be accommodated in each layer. The connection wires, in turn, run in the warp direction. At the desired height, the two layers 67, 68 are separated from each other and folded over, as shown, to produce the desired F-shaped structure.

Figure 10:
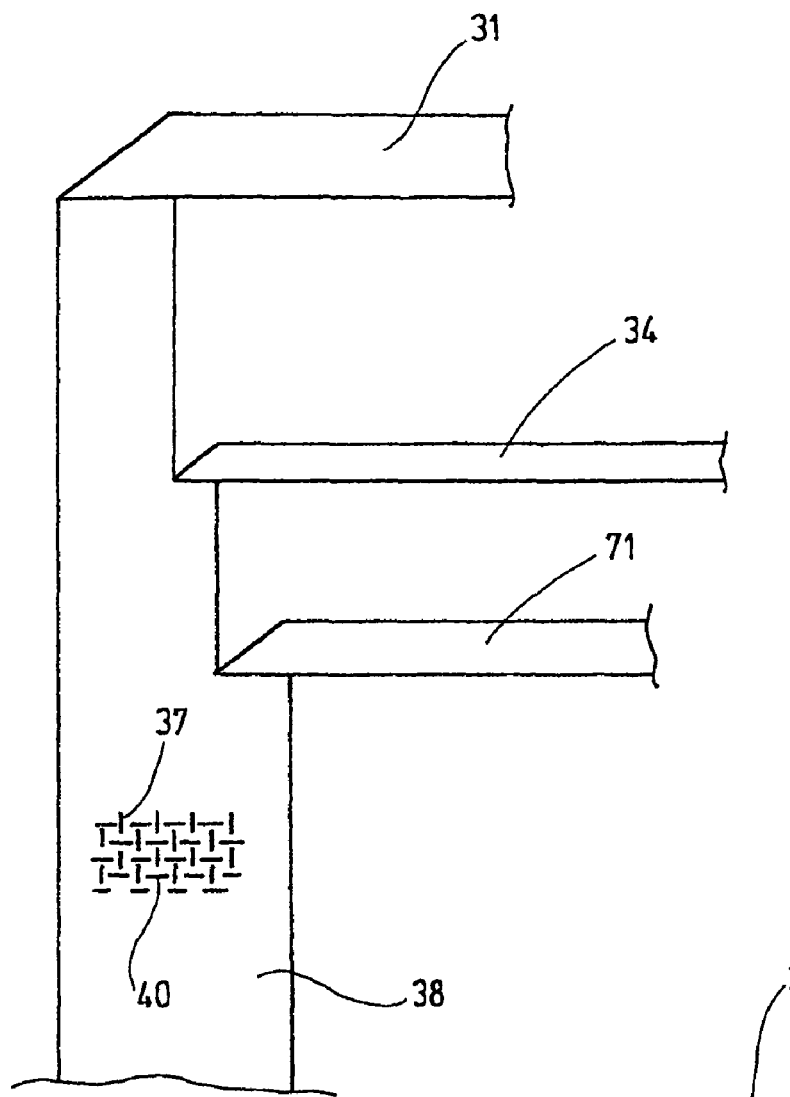

FIG. 10 depicts how not just two outlets 31, 34, but more outlets, such as three outlets 31, 34, 71, are possible by means of the striplike cable 38. In this case, the strip after being woven is separated in the lengthwise direction in the desired manner, parallel to the warp threads, and folded over.

Figure 11:
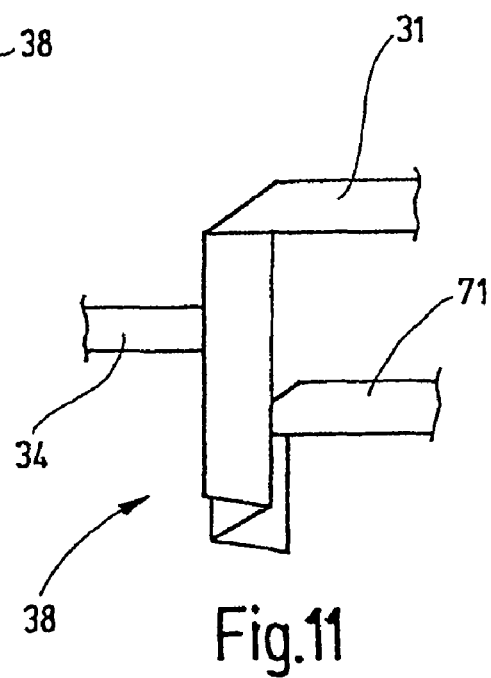
Figure 12:
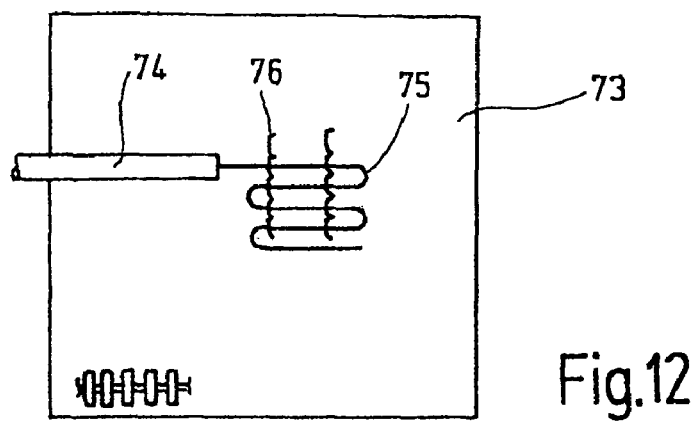
FIGS. 12-16 are depictions of alternative forms of fastening means for securing a wire onto a textile structure of a garment in accordance with the invention.

According to FIG. 11, a relatively broad strip 38, whose overall width when lying flat is as wide as the sum of the widths of the individual branch lines 31, 34, 71, is folded in accordion fashion. This reduces the width of the striplike cable 38 to the width of the broadest branch, for example, branch 31. Furthermore, a "wiring harness" can be created in which the individual branch lines 31, 34, 71 lead off from different sides. A leading off from the same side, i.e., an F with three arms, also can be easily achieved.

FIGS. 12-17 illustrate a number of methods for combining the conductor of an insulated wire with a textile backing 73. An insulated conductor 74 is stripped of its insulation for a distance so that the wire 75 contained inside the conductor 74 is exposed. Using sewing thread 76, the bare piece of wire is sewn onto the electrically nonconductive textile substrate 73.

Figure 13:
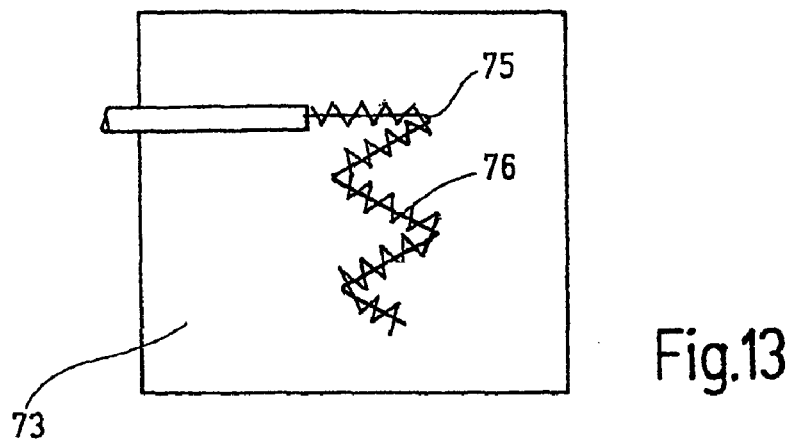
Figure 14:
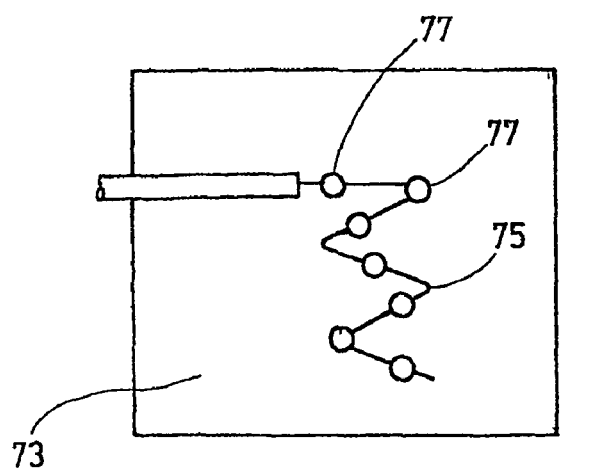

According to FIG. 13, the stripped wire 75 is stitched firmly to the backing by means of a thread 76. In the embodiment of FIG. 14, the bare wire 75 is secured by means of glue spots 77. Instead of separate glue spots 77, if the textile substrate contains threads susceptible of hot melt gluing, the stripped wire 75 can also be secured to the substrate by melting these threads to the glue state. The melting can be achieved by heat or by ultrasound.

Figure 15:
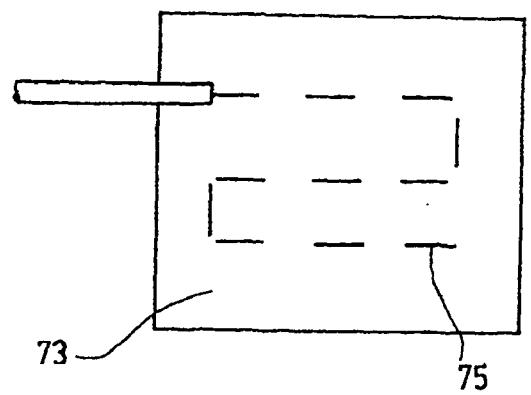
Figure 16:
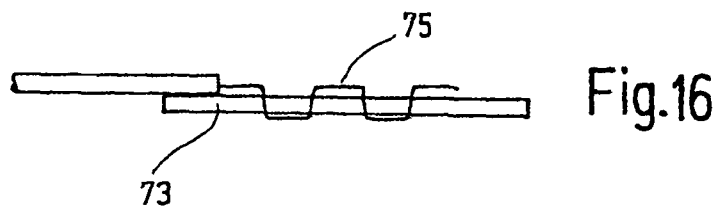

FIGS. 15 and 16 illustrate how the stripped wire 75 is sewn as a thread into the substrate 73. As FIG. 16 reveals, the wire 75 appears alternate on either side of the textile substrate. The textile substrate can be woven, knitted, or nonwoven.

Figure 17:
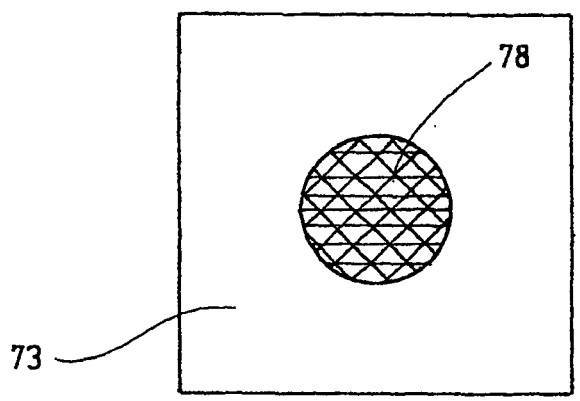
FIG. 17 is a top view illustrating the surface structure of an illustrative sensor.
Figure 18:
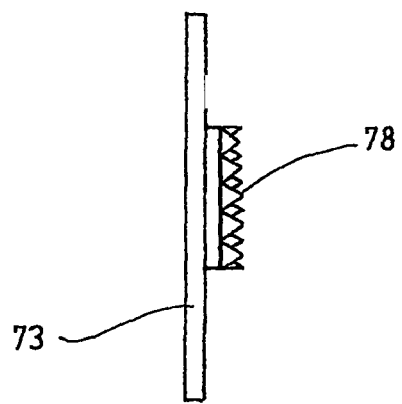
FIG. 18 is a side view of the sensor shown in FIG. 17.

The above-mentioned sensors made from elastomer lie flat against the skin and largely seal off this portion of the skin. Skin transpiration can only emerge underneath the sensor with difficulty. To improve the aeration and the draining off of sweat, the sensor surface can be structured as shown in FIG. 17. It can consist, for example, of a plurality of small pyramids 78 whose tips are directed at the skin. Under moderate pressure, channels are formed between the tips through which sweat can drain off. Beneath the surface shown, the wire 75 used for the contacting can be arranged as in FIGS. 12-16, or by using a Jacquard technique, as explained by means of FIG. 6.

The elongation sensor as depicted in FIG. 2 consists of an elastomer which is filled with electrically conductive particles. However, hydrogels can also be used as an elongation-dependent sensor. Such a sensor contains a hydrogel which is filled with an electrolyte solution. Water is stored in a three-dimensional cross-linked matrix of hydrophilic water-insoluble polymers and is virtually immobilized in this way. Suitable hydrogels are polymethacrylates, polyphenylpyrrolidones, or polyphenylalcohol. A water-soluble salt is added to the water stored in the hydrogel layer in order to achieve an ionic conductivity for the water. Suitable as the salt is AgCl, as well as any other physiologically safe metal salt, for example, table salt. A change in cross section caused by a change in length due to stretching or pressure influences the conductivity. The resistance measured is an indication of the strain to which the sensor outfitted with a hydrogel is subjected.

The hydrogel is located as a kind of filler between two water-tight and ion-tight, highly elastic layers, similar to that shown for the conductive layer 48 in FIG. 3. Thus, the construction of a sensor based on a hydrogel corresponds to the construction shown in FIG. 3, using the hydrogel in place of the conductive elastomer 48. Silicone can be used as the elastomer. The benefit of hydrogels is that, depending on the degree of cross linking, one can achieve a very soft texture, conveniently worn on the body.

The garment according to the invention has been described in detail in connection with a body suit. The body suit represents the preferred embodiment. However, it is also possible to fasten the indicated sensors on vests, T-shirts, or undershirts, as long as these garments are worn closely against the body.

In a body suit, one or two belts which can stretch in the lengthwise direction run transversely to the longitudinal axis of the wearer. Elongation measuring strips are arranged in these belts. Electrodes for tapping the action currents of the heart or for measuring the skin resistance are located on the outer side of the belts, making contact with the body.

The invention claimed is:

1. A garment comprising:
 a body portion to be worn on the body of a user,
 at least one sensor (25, 26, 27, 28, 29, 30) for detecting a bodily function of the user,
 said sensor (25, 26, 27, 28, 29, 30) being fastened to the garment body portion such that it is properly positioned in relation to the body of a user for providing an output electrical signal indicative of a detected bodily function,
 said body portion being formed at least in part by a woven or knitted non-conductive fabric material, and
 at least one insulated single electrical conductor electrically connecting each sensor to an electrical connector, and each said insulated single electrical conductor being integrated into the fabric material as a floating thread or a stationary thread woven within non-conductive fabric material.

2. The garment of claim 1 in which said sensor is effective for detecting at least one of a skin resistance, respiration, pulse, action currents of the heart, or body temperature of the user.

3. The garment of claim 1 in which said body portion is a body suit for enclosing the chest and abdomen of the body of the user, and said body suit being formed with a neck cut out, two arm cutouts (7, 8), and two leg cutouts.

4. The garment of claim 3 in which said body suit can be opened in a lengthwise direction to facilitate placing the body suit on and removing the body suit from the body of a user.

5. The garment of claim 3 in which said body suit has at least one crotch piece (6) formed as a part of the body portion for positioning across a crotch of the body of the user.

6. The garment of claim 3 in which said body suit is formed with sleeves (9, 10).

7. The garment of claim 1 in which said body portion is a vest.

8. The garment of claim 1 in which said body portion is a T-shirt.

9. The garment of claim 1 in which said body portion is formed with straps for fixedly maintaining the body portion in place on the body of a user.

10. The garment of claim 1 in which said body portion is in the form of trousers (63) having retention straps.

11. The garment of claim 10 in which said retention straps are in the form of suspenders (64, 66) with a cross band (65) therebetween.

12. The garment of claim 1 in which said body portion has a section that can stretch in at least one direction, and said sensor is positioned on said section of said body portion that can stretch in said at least one direction.

13. The garment of claim 1 in which said body portion is formed of a multi-layered woven fabric.

14. The garment of claim 13 in which said multilayered woven fabric is a knitted fabric (23).

15. The garment of claim 1 in which said sensor (29, 26) has an electrical resistance value that changes in response to strain on the sensor.

16. The garment of claim 1 in which said sensor (29, 30) has a specific resistance value of about 25 ohm cm.

17. The garment of claim 1 in which said sensor (26, 27, 28) is a flexible sensor with an electrical resistance value that remains substantially constant.

18. The garment of claim 1 in which said sensor (25, 26, 27, 28, 29, 30) is made of an elastomeric material (53) in which conductive particles (52) are embedded.

19. The garment of claim 18 in which said conductive particles (52) are carbon particles.

20. The garment of claim 18 in which said conductive particles (52) are carbon particles each having a diameter between 0.01 and 10 μm.

21. The garment of claim 18 in which said conductive particles (52) are conductive metal particles each having a diameter between 0.01 and 10 μm, and the metal of said particles includes at least one of the substances of Al, Cu, Ag, Fe, Ni, or Ti.

22. The garment of claim 19 in which said carbon particles comprise a volume of between 30 and 60% of the material of the sensor.

23. The garment of claim 1 in which said sensor includes an elastomer (53) that is a skin-tolerable material.

24. The garment of claim 1 in which said sensor includes an elastomer (53) that is a non-allergenic material.

25. The garment of claim 1 in which said sensor includes an elastomer (53) that is stretchable more than a substrate surface on which the sensor is placed on the body portion.

26. The garment of claim 1 in which said sensor includes an elastomer (53) that is one of a fluoropolymer, polyurethane or silicone.

27. The garment of claim 1 in which said sensor (29, 30) has an insulating layer (51) on a single side thereof.

28. The garment of claim 1 in which said sensor (29, 30) has an insulating layer (47, 51) on all sides thereof.

29. The garment of claim 1 in which said sensor includes a layer of insulating material on at least one side and an active layer of material containing a conductive filler (52).

30. The garment of claim 1 in which said sensor (29, 30) is in the shape of flat strip, having a transverse dimension smaller relative to a lengthwise direction.

31. The garment of claim 1 in which said sensor (25, 26, 27, 28) has a round disk-like shape.

32. The garment of claim 1 in which said sensor (25, 26, 27, 28, 29, 30) is made of a material that is not sensitive to body sweat.

33. The garment of claim 1 in which said sensor (25, 26, 27, 28, 29, 30) is made of a material that is not sensitive to fabric care products and detergents.

34. The garment of claim 1 in which said sensor (25, 26, 27, 28, 29, 30) is made of a material that is warm-water resistant.

35. The garment of claim 1 in which said sensor (25, 26, 27, 28, 29, 30) is made of a material that is hot-water resistant.

36. The garment of claim 1 in which said sensor (25, 26, 27, 28, 29, 30) is made of a material that can withstand sterilization in an autoclave.

37. The garment of claim 1 in which said sensor contains a hydrogel.

38. The garment of claim 1 in which said sensor has a structured surface.

39. The garment of claim 1 in which said sensor (25, 26, 27, 28, 29, 30) is arranged on at least one belt (31, 34) of the body portion.

40. The garment of claim 39 in which said belt (31, 34) has a part located on an inner side of the garment.

41. The garment of claim 39 in which said belt is made of a stretchable material.

42. The garment of claim 39 in which said belt (31, 34) is in the form of a flat tube within which the sensor (29, 30) is carried.

43. The garment of claim 39 in which said belt (31, 34) is formed as a flat tube on which the sensor is carried.

44. The garment of claim 39 in which said belt is formed of a knitted fabric.

45. The garment of claim 39 in which said belt extends from said body portion transversely to a longitudinal or upright axis of the body of a user.

46. The garment of claim 39 in which said body portion includes first and second belts which together form an F-shaped structure.

47. The garment of claim 46 in which said first and second belts run parallel to each other and each belt supports at least one sensor (25, 26, 27, 28, 29, 30).

48. The garment of claim 39 in which said belt (31, 34) has a first segment sewn to said body portion and a second segment freely movable relative to the first segment and having an anchoring device (33, 36) for releasably securing the second segment to the body portion.

49. The garment of claim 39 in which said body portion has arm cutouts (7, 8) and said belt is adapted for extending about a chest region of the body of a user below the arm cutouts.

50. The garment of claim 49 including a second belt (34) for extending in the region of the abdomen of the body of a user and having a sensor for detecting abdominal breathing.

51. The garment of claim 48 in which said first segment of said belt (31, 34) extends into a tube (41) formed in the body portion that runs in a lengthwise direction of the upright axis of the body of the user.

52. The garment of claim 1 in which said insulated conductors each form a warp thread in said fabric (38).

53. The garment of claim 1 in which said insulated single conductor (37) is integrated into knitted non-conductive fabric of the body portion as a stationary thread.

54. The garment of claim 1 in which each said insulated single conductor is integrated into said non-conductive fabric material as a floating thread.

* * * * *